United States Patent [19]
Sato et al.

[11] Patent Number: 5,916,904
[45] Date of Patent: *Jun. 29, 1999

[54] ANTIMICROBIAL AGENT

[75] Inventors: Masaru Sato, Saitama; Shigeru Souda, Ibaraki, both of Japan

[73] Assignee: Eisai Co., Ltd., Japan

[*] Notice: This patent issued on a continued prosecution application filed under 37 CFR 1.53(d), and is subject to the twenty year patent term provisions of 35 U.S.C. 154(a)(2).

[21] Appl. No.: 08/670,213

[22] Filed: Jun. 20, 1996

Related U.S. Application Data

[63] Continuation of application No. 08/379,124, Jan. 27, 1995, abandoned, which is a continuation of application No. 08/077,193, Jun. 16, 1993, abandoned.

[30] Foreign Application Priority Data

Aug. 21, 1992 [JP] Japan .................................. 4-244042

[51] Int. Cl.$^6$ .................................................. A61K 31/44
[52] U.S. Cl. ............................................................ 514/338
[58] Field of Search ............................................... 514/338

[56] References Cited

U.S. PATENT DOCUMENTS 5,013,743  5/1991  Iwahi ...................................... 514/338

FOREIGN PATENT DOCUMENTS

| 0 268 956 | 6/1988 | European Pat. Off. . |
| 0 382 489 | 8/1990 | European Pat. Off. . |
| A-3-48680 | 1/1991 | Japan . |

OTHER PUBLICATIONS

Cancer, Dec. 15, 1990 vol. 66, pp. 2569–2574 Correa et al Helicobacter pylori and Gastic Carcinoma.
Lambert et al Gastroenterology vol. 92 No. 5, part Abstracts of Papers p. 1488 (1987) "Role of Campylobacter Phyoridis in Non–Ulcer Dyspepsia".
Abstract WPI Acc No: 91–106284/15 of JP 3048680.

*Primary Examiner*—Alan Siegel
*Attorney, Agent, or Firm*—Nixon & Vanderhye

[57] ABSTRACT

An ulcer and/or gastritis are prevented, improved or treated by administering a pharmacologically effective amount of the compound having the below shown formula (I) or (II) or a pharmacologically acceptable salt thereof to a mammal suffering from such a disease.

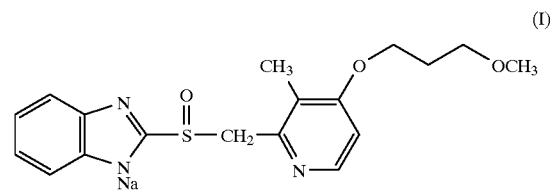

(I)

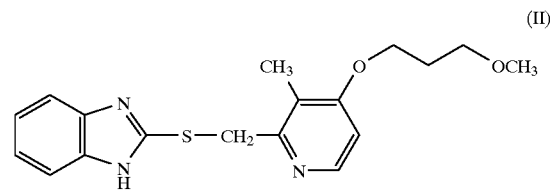

(II)

9 Claims, No Drawings

ANTIMICROBIAL AGENT

This is a continuation of application Ser. No. 08/379,124, filed Jan. 27, 1995, now abandoned which is a continuation of 08/077,193 filed Jun. 16, 1993, now abandoned.

The invention relates to in antimicrobial agent, antibiotic, anti-bacterial medicine which prevents, improves and therapeutically treats a disease caused by *Campylobacter pylori,* called hereinafter *C. pylori.* The organism is a microaerophilic, gram-negative spirillar rod and it is thought to participate in recurrent, peptic ulcer, gastric ulcer, duodenal ulcer and gastritis.

STATEMENT OF PRIOR ART

Many substances have been used for prevention, treatment or cure of peptic ulcer, gastric ulcer, duodenal ulcer or gastritis. Especially, histamine $H_2$-receptor antagonists such as cimetidine or ranitidine have been widely used. Histamine $H_2$-receptor antagonists quickly improve damaged stomach and duodenal mucous membrane, and they reduce subjective symptoms such as stomach pain immediately. However, a problem remains that these diseases will recur very often after they have healed and the medication has been stopped. The reason isn't entirely clear, but after the discovery that *C. pylori* was detected from the stomach mucous membrane biopsy sample of peptic ulcer patients in 1979, it is thought that there's a close relationship between *C. pylori* and peptic ulcer, gastric ulcer, duodenal ulcer and gastritis. In 1989, it was proposed to rename *C. pylori* to *Helicobacter pylori* by further research in the viewpoint of bacteriology and bacterial taxology. Therefore, *C. pylori* is also called *H. pylori.*

It is reported in the Medical Journal of Australia, volume 142, pages 436–439, 1985 and American Journal of Gastroentelology, volume 82, pages 192–199, 1987 that healthy volunteers gives *C. pylori* orally suffered from acute gastritis. Gastroentelology, volume 94, pages 33–40, 1988 showed that the injured gastric tissue was found to have been improved when *C. pylori* was eradicated by administration of an antibiotic substance. Such relationship between *C. pylori* and, peptic ulcer, gastric ulcer, duodenal ulcer and gastritis is at present noticed.

Lancet, pages 1437–1442, 1988 reported that among *C. pylori* positive peptic ulcer patients, the relapse rate is higher than negative ones. This shows that prevention and treatment of recurrent peptic ulcer, gastric ulcer, duodenal ulcer and gastritis required eradication of *C. pylori.*

In the state of art, medicines which can eradicate *C. pylori* include antibiotics such as ampicillin, cefalexin, ofloxacin, minocycline and roxithromycin and medicaments for gastritis or gastric ulcer such as plaunotol, sofalcone, benexate hydrochloride and colloidal bismuth subcitrate.

Among these substances which can clear *C. pylori,* prior medicines for gastritis and gastric ulcer provide too weak an eradication activity at the usual dosage of administration. Antibiotics mentioned above have good efficacy against *C. pylori,* but some side-effects such as allergy or diarrhoea will occur often, and then, after long term administration, it sometimes causes severe irreversible adverse reactions such as hematological disorders or gastrointestinal disorders. And it produces resistant bacteria easily. From the clinical point of view, a good medicine is expected for reliable prevention and therapy, for a long term medication of recurrent ulcer and gastritis with safety. The research has continued for a medicine which could eradicate *C. pylori* in a usual dosage of administration with safety in the long term medication.

JP-A 2-209809, corresponding to U.S. Pat. No. 5,093,342 discloses 5-Methoxy-2-[(4-methyl-3,5-dimethyl-2-pyridinyl)methylsulfinyl]-1H-benzimidazole, called omeprazole, or a salt thereof, being an acid secretion-inhibiting medicine for gastritis and gastric ulcer, has antibiotic activity against *C. pylori* 8005 one of the clinical isolates. JP-A 3-173817, corresponding to U.S. Pat. No. 5,013,743 discloses the compounds (1) to (14) shown below having antibiotic activity against *C. pylori* NCTC-11916 and NCTC-11637 the standard strains and *C. pylori* PCL-56, CPY-0011-1, KS-13, CLO-1 and CLO-6 the clinical isolates.
1) 2-[(3-Methyl-4-(2,2,2-trifluoroethoxy)pyrid-2-yl) methylsulfinyl]-1H-benzimidazole
2) 2-(3,5-Dimethyl-4-methoxypyrido-2-yl)methylsulfinyl-5-methoxy-1H-benzimidazole
3) 2-[(3-Methyl-4-(2,2,3,3,3-pentafluoropropoxy)pyrid-2-yl)methylsulfinyl]-1H-benzimidazole
4) 2-[(3-Methyl-4-(2,2,3,3-tetrafluoropropoxy)pyrid-2-yl) methylsulfinyl]-1H-benzimidazole
5) 2-[{3-Methyl-4-(2,2,3,3,4,4-hexafluorobutoxy)pyrid-2-yl)methylsulfinyl]-1H-benzimidazole
6) 2-[{3-Methyl-4-(2,2,2-trifluoroethoxy)pyrid-2 -yl) methylthio]-1H-benzimidazole
7) 2-[{(4-Isobutoxy)pyrid-2-yl)methylthio]-1H-benzimidazole
8) 2-[{(4-Isobutoxy)pyrid-2-yl)methylthio]-5-trifluoromethyl-1H-benzimidazole
9) 2-[{(4-Isoprotoxy)pyrid-2-yl)methylthio]-5-trifluoromethyl-1H-benzimidazole
10) 2-[{(4-(2'-Propenyl)oxy}pyrid-2-yl)methylthiol-5-trifluoromethyl-1H-benzimidazole
11) 2-[((4-Propargyl)oxypyrid-2-yl)methylthio]-5-trifluoromethyl-1H-benzimidazole
12) 2-[{3-Methyl-4-(2,2,3,3-tetrafluoropropoxy)pyrid-2-yl}methylthio]-1H-benzimidazole
13) 2-[{3-Methyl-4-(2,2,3,3,3-pentafluoropropoxy)pyrid-2-yl}methylthio]-1H-benzimidazole
14) 2-[{3-Methyl-4-(2,2,3,3,4,4-hexafluorobutoxy)pyrid-2-yl}methylthio]-1H-benzimidazole JP-A 3-48680 discloses the below shown compound being antibiotic to *C. pylori,* failing to show tested strains.
1) 2-[3-Methyl-4-(1-methyl-2-piperidyl)methoxy-2-pyridyl]methylthio-1H-benzimidazole
2) 2-[3-Methyl-4-(3-morpholinopropoxy)-2-pyridyl] methylthio-1H-benzimidazole
3) 2-[3-Methyl-4-(2-piperidinoethoxy)-2-pyridyl] methylthio-1H-benzimidazole
4) 2-[3-Methyl-4-{2-(2-oxo-1-pyrrolidinyl)ethoxy}-2-pyridyl]methylthio-1H-benzimidazole
5) 2-[3-Methyl-4-(2-morpholinoethoxy)-2-pyridyl] methylthio-1H-benzimidazole
6) 2-[3-Methyl-4-(3-piperidinopropoxy)-2-pyridyl] methylthio-1H-benzimidazole
7) 5-Methoxy-2-[3-methyl-4-(2-morpholinoethoxy)-2-pyridyl]methylthio-1H-benzimidazole
8) 5-Methoxy-2-[3-methyl-4-{2-(N-benzyl-N-methylamino)ethoxy}-2-pyridyl]methylthio-1H-benzimidazole
9) 2-{3-Methyl-4-[2-(N-methyl-N-(2-phenylethyl) amino}ethoxy}-2-pyridyl]methylthio-1H-benzimidazole
10) 2-[3-Methyl-4-[2-(N-methyl-N-(3-phenylpropyl) amino}ethoxy]-2-pyridyl]methylthio-1H-benzimidazole
11) 2-[3-Methyl-4-{2-(N-benzyl-N-ethylamino)ethoxy}-2-pyridyl]methylthio-1H-benzimidazole
12) 2-[3-Methyl-4-{2-(N-benzyl-N-propylamino)ethoxy)-2-pyridyl]methylthio-1H-benzimidazole
13) 2-[3-Methyl-4-[2-{N-methyl-N-(4-methylbenzyl) amino}ethoxy]-2-pyridyl]methylthio-1H-benzimidazole 14) 2-[3-Methyl-4-[2-{N-(4-chlorobenzyl)-N-methylamino}ethoxy]-2-pyridyl]methylthio-1H-benzimidazole 15) 2-[3-Methyl-4-[2-{N-(4-bromobenzyl)-N-methylamino}ethoxy]-2-pyridyl]methylthio-1H-benzimidazole 16) 2-[3-Methyl-4-{2-(1,2,3,4-tetrahydrolsoquinoline-2-yl)ethoxy}-2-pyridyl]methylthio-1H-benzimidazole 17) ½ magnesium salt of 2-[3-methyl-4-{2-(N-benzyl-N-methylamino)ethoxy}-2-pyridyl]methylsulfinyl-1H-benzimidazole 18) ½ magnesium salt of 2-[3-Methyl-4-[2-{N-methyl-N-(4-methylbenzyl)amino}ethoxy]-2-pyridyl]methylsulfinyl-1H-benzimidazole 19) ½ magnesium salt of 2-[3-Methyl-4-[2-{N-(4-bromobenzyl)-N-methylamino}ethoxy]-2-pyridyl]methylsulfinyl-1H-benzimidazole 20) 2-[3-Methyl-4-[2-(1,2,3,4 -tetrahydroisoquinoline-2-yl)ethoxy]-2-pyridyl]methylsulfinyl-1H-benzimidazole 21) 2-[3-Methyl-4-[2-(N-benzyl-N-methylamino)ethoxy]-2-pyridyl]methylsulfonyl-1H-benzimidazole 22) 2-[3-Methyl-4-[2-(N-methyl-N-(4-methylbenzyl)amino)ethoxy]-2-pyridyl]methylsulfonyl-1H-benzimidazole In the treatment of diseases caused by C. pylori, it's necessary to have excellent activity against a broad spectrum of C. pylori including standard strains and clinical isolates. The antibiotics effective against C. pylori have minimum inhibitory concentration called M.I.C. (μg/ml) in the range of less than 1 μg/ml. Therefore, whether a compound has a M.I.C. in that range or not is a criterion to evaluate its clinical efficacy against C. pylori.

From the above omeprazole disclosed in JP-A 2-209809 and JP-A 3-173817 lacks sufficient antibiotic activity. Among the other 14 compounds shown in JP-A 3-173817, compounds (12), (13) and (14) only are the antibiotics in the respect of activity against all the tested strains.

JP-A 3-48680 shows that compounds have an MIC of 1 microgram per ml or less to only one tested strain. It is not expected from the listed data that they will have antibiotic activity widely against many strains.

2-[(4-(3-Methoxypropoxy)-3-methylpyridine-2-yl)-methylsulfinyl]-1H-benzimidazole (I) and 2-[(4-(3-Methoxypropoxy)-3-methylpyridine-2-yl)-methylthio]-1H-benzimidazole (II) are known in JP-A 1-6270, corresponding to EP-A 268 956 as acid secretion inhibitor. They can be prepared according to Examples 32 and 31, respectively, disclosed in JP-A 1-6270.

DISCLOSURE OF THE INVENTION

The inventors have investigated 2-[(4-(3-Methoxypropoxy)-3-methylpyridine-2-yl)-methylsulfinyl]-1H-benzimidazole (I) and 2-[(4-(3-Methoxypropoxy)-3-methylpyridine-2-yl)-methylthio]-1H-benzimidazole (II) and have found them to have the same C. pylori-eradicating activity as an antibiotic substance. The two compounds of the invention have the following chemical structures:

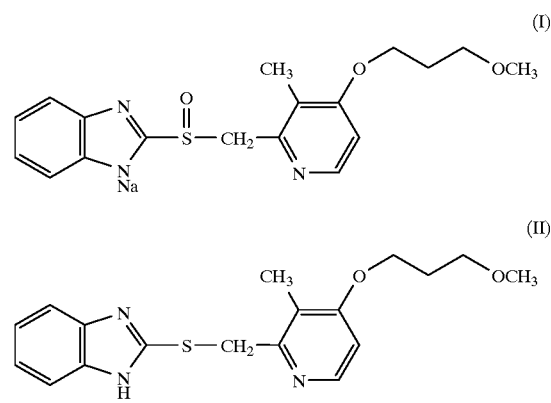

The invention provides a method for preventing, improving or treating an ulcer and/or gastritis by administering a pharmacologically effective amount of the compound having the above shown formula (I) or (II) or a pharmacologically acceptable salt thereof to a mammal suffering from such a disease.

It is preferable that the mammal is human being, the ulcer is a peptic ulcer, the ulcer is a gastric ulcer, and the ulcer and gastritis are recurrent.

The invention moreover provides a method for eradicating C. pylori from the mucous membrane of the stomach of a patient suffering from a ulcer, duodenal ulcer or gastitis by administering a pharmacologically effective amount of the compound having the formula (I) or (II) or a pharmacologically acceptable salt thereof to the patient; a method for eradicating C. pylori from the mucous membrane of the stomach of a patient suffering from a gastric ulcer, duodenal ulcer or gastritis by administering a pharmacologically effective amount of the compound having the formula (I) or (II) or a pharmacologically acceptable salt thereof to the patient; a method for preventing, improving or treating a disease caused by C. pylori by administering a pharmacologically effective amount of the compound having the formula (I) or (II) or a pharmacologically acceptable salt thereof to a mammal suffering from the disease; a method for preventing recurring of a disease caused by C. pylori by administering a pharmacologically effective amount of the compound having the formula (I) or (II) or a pharmacologically acceptable salt thereof to a mammal suffering from the disease, and a method for restraining the adverse activity of C. pylori to cause a peptic disease by administering a pharmacologically effective amount of the compound having the formula (I) or (II) or a pharmacologically acceptable salt thereof to a mammal suffering from the disease.

The invention further provides an antimicrobial medicine or agent comprising the compound having the formula (I) or (II) to prevent, improve or treating an ulcer and/or gastritis and the use of the compound for manufacturing said medicine or agent.

In the invention, the pharmaceutically acceptable salt of the compound (I) or (II) includes an addition salt thereto by an inorganic acid such as hydrochloric acid, sulfuric acid, hydrobromic acid, hydrolytic acid, nitric acid, perchloric acid and phosphoric acid, an addition salt thereto by an organic acid such as citric acid, maleic acid, fumaric acid, succinic acid, methanesulfonic acid, benzenesulfonic acid and p-toluenesulfonic acid, an addition salt thereto by a metal such as sodium, potassium, calcium and magnesium. Sodium salt is most preferable.

The invention provides medicine which is effective for the C. pylori eradication having the same effect as antibiotics. The compounds of the invention can be administered for a long time with safety, without side effects. It is pharmacologically effective and clinically useful to recurrent ulcers and gastritis.

The compounds of the invention have the following physical properties.

The physical property of 2-[(4-(3-Methoxypropoxy)-3-methylpyridine-2-yl)-methylsulfinyl]-1H-benzimidazole (I)

molecular formula: $C_{18}H_{20}N_3O_3S$
molecular weight: 358.44
property: white crystalline The physical property of 2-[(4-(3-Methoxypropoxy)-3-methylpyridine-2-yl)-methylthio]-1H-benzimidazole (II)
molecular formula: $C_{18}H_{20}N_3O_2S$
molecular weight: 342.44
property: pale yellow crystalline Pharmacological Test Standard strains and clinical isolates of C. pylori derived from the mucous membrane of the stomach were used and determined in vitro according to the agar dilution method determined by Nihon Kagaku Ryoho Gakkai (English name: Japan Society of Chemotherapy).

Sodium salt of 2-[(4-(3-Methoxypropoxy)-3-methylpyridine-2-yl)-methylsulfinyl]-1H-benzimidazole (I) was dissolved in a sterilized water. 2-[(4-(3-Methoxypropoxy)-3-methylpyridine-2-yl)-methylthio]-1H-benzimidazole (II) and, as controls, omeprazole, 5-Methoxy-2-[(4-methoxy-3,5-dimethyl-2-pyridinyl)methylthio]-1H-benzimidazole and 2-[(3-Methyl-4-(2,2,2-trifluoroethoxy)-pyrid-2-yl)methylthio]-1H-benzimidazole were dissolved separately in a 1% dimethylsulfoxide solution. As an antibiotic substance control, roxithromycin as macrolides, ampicillin as penicillins, ofloxacin as newquinolones were dissolved in a buffer solution of acetic acid having a pH of 5.0, a sterilized water and an 1N aqueous solution of NaOH, respectively. Test plates were prepared by adding 7% horse blood to Brucella agar named by BBL Microbiology Systems (tradename), available from Bector Dickson and Company. The incubation was conducted at 37° C. at pH of 7.0 for 3 days under the microaerophilic condition using Canpipack (tradename) available from Bector Dickson and Company. MIC was determined in unit of microgram per ml. Test results are shown in Table 1. NCTC11637 and NCTC11916 are standard strains. The other references indicate clinical isolates.

The test result is shown in terms of the antibiotic activity (MIC) in unit of microgram/ml. obtained in vitro against C. pylori. The tested compounds are (I) sodium salt of 2-[(4-(3-Methoxypropoxy)-3-methylpyridine-2-yl}methylsulfinyl]-1H-benzimidazole, (II) 2-[{4-(3-Methoxypropoxy)-3-methylpyridine-2-yl}methylthio]-1H-benzimidazole, (III) 5-Methoxy-2-[{(4-methoxy-3,5-dimethyl-2-pyridinyl)methyl}sulfinyl]-1H-benzimidazole (omeprazole). (IV) 5-Methoxy-2-{(4-methoxy-3,5-dimethyl-2-pyridinyl)methylthio}-1H-benzimidazole, (V) 2-[{3-Methyl-4-(2,2,2-trifluoroethoxy)pyrid-2-yl}methylthio]-1H-benzimidazole, (VI) roxithromycin (RXM), (VII) ampicillin (ABPC), (VIII) ofloxacin (OFLX).

TABLE 1

| Tested strain | Compunent | | | | | | | |
|---|---|---|---|---|---|---|---|---|
| | (I) | (II) | (III) | (IV) | (V) | (VI) | (VII) | (VIII) |
| NCTC11637 | 3.13 | 0.8 | 50 | 25 | 25 | 0.4 | 0.4 | 0.8 |
| NCTC11916 | 3.13 | 0.2 | 25 | 12.5 | 12.5 | 0.1 | 0.05 | 0.8 |
| EI-2 | 3.13 | 0.4 | 25 | 25 | 25 | 0.2 | 0.4 | 0.8 |
| EI-5 | 3.13 | 0.2 | 50 | 25 | 12.5 | 0.2 | 0.4 | 0.8 |
| EI-36 | 6.25 | 0.4 | 25 | 12.5 | 12.5 | 0.2 | 0.2 | 0.8 |
| EI-46 | 3.13 | 0.4 | 25 | 12.5 | 12.5 | >100 | 0.05 | 3.13 |
| EI-391 | 3.13 | 1.56 | 50 | 25 | 12.5 | 50 | 0.1 | 25 |
| EI-393 | 3.13 | 1.56 | 50 | 25 | 25 | 0.2 | 0.1 | 0.8 |
| EI-397 | 3.13 | 1.56 | 50 | 25 | 25 | 0.2 | 0.1 | 0.8 |
| EI-429 | 1.56 | 1.56 | 25 | 25 | 25 | 0.2 | 0.2 | 0.8 |
| EI-467 | 1.56 | 1.56 | 50 | 12.5 | 12.5 | 0.2 | 0.05 | 0.4 |
| EI-612 | 0.4 | 0.8 | 25 | 12.5 | 6.25 | 0.2 | 0.05 | 0.8 |
| EI-925 | 3.13 | 0.4 | 25 | 12.5 | 12.5 | 0.2 | 0.2 | 0.4 |
| EI-930 | 3.13 | 0.4 | 25 | 12.5 | 12.5 | 0.4 | 0.4 | 0.8 |
| EI-933 | 3.13 | 0.8 | 25 | 12.5 | 12.5 | 0.1 | 0.05 | 0.4 |

It is noted from the test results that the compounds of the invention are superior to the known compounds such as omeprazole disclosed in JP-A 2-209809 and lansoprazole derivatives disclosed in JP-A 3-173817. The compounds of the invention evidently provide an equivalent C. pylori eradicating activity to antibiotics. Since the compounds of the invention are not of antibiotic compounds, the compounds of the invention work effectively against resistant bacteria such as clinically isolated strains shown in Table, EI-46 and EI-391. This is the reason they provide the antibiotic activity against a wider variety of bacteria than antibiotic substances. They can be administered continuously for long term. They have been found at a concentration of 100 micrograms per ml, not to inhibit other gram-positive and gram-negative bacilli from growing. This shows the fact that they exhibit antibiotic activity selectively to C. pylori.

Acute Toxicological Test

The compound (I) of the invention was administered Intravenously or orally one time, with a carrier of saline, to Slc:SD rats and Slc:ICR mouse, each being 7 or 8 weeks old, in a group consisting of five males and five females, to determine $LD_{50}$ values. Results are shown in Table 2.

Acute toxicity of the compound (I) is shown in terms of $LD_{50}$ in unit of mg/kg.

TABLE 2

| medication | rats | | mouce | |
|---|---|---|---|---|
| process | male | female | male | female |
| intravenous | 157 mg/Kg | 152 mg/Kg | 220 mg/Kg | 237 mg/Kg |
| oral | 1447 mg/Kg | 1332 mg/Kg | 1206 mg/Kg | 1012 mg/Kg |

The obtained $LD_{50}$ values are 5000 times as much as a clinical dosage for oral administration and for this reason the compounds of the invention are found to be safe, that is, providing no toxicological influence.

Technological Advances of The Invention

It is evident from the above test data that the compounds of the invention are antibiotic against C. pylori as antibiotic substances and therefore can work pharmacologically to prevent, improve and therapeutically treat recurrent ulcers and gastritis caused by C. pylori. They can prevent, improve and therapeutically treat peptic ulcers, controlling secretion of gastric acid, and moreover prevent, improve and therapeutically treat recurrent ulcers and gastritis caused by C.

pylori, with safety. They can be administered continuously for a long term, without combination of another antibiotic substance. The compounds can be used as an antibiotic medicine.

Application of The Invention

The compounds of the invention can be administered, without any limitation, in any of the normal ways. Which way and how much for medication depend on the condition of the patient, the kind of ulcer and gastritis, a degree or extent of the disease, age of a patient and functions of heart, liver and kidney. It is preferable according to the invention that the patients are dosed orally in an amount of 0.01 to 100 mg a day, more preferably 0.1 to 80 mg, further preferably 0.1 to 60 mg, most preferably 5 to 40 mg. The oral medication can be in the form of a powder, granule, tablet or capsule. They can be prepared with a normally used carrier according to prior methods. Preferably according to the showing in JP-A 1-290628 and JP-A 2-22225, corresponding to U.S. Pat. No. 5,035,899. The preparation may further include a forming filler, a binder, a disintegrating agent, a lubricant, a colorant, a corrigent, a taste-improver and or a smell-improver.

The filler includes lactose, corn starch, white sucrose, glucose, mannitol, sorbitol, crystalline cellulose and silicon dioxide; the binder, polyvinyl alcohol, polyvinyl ether, ethylcellulose, methylcellulose, acacia, tragacanth, gelatin, shellac, hydroxypropylcellulose, hydroxypropyl starch and polyvinylpyrrolidone; the disintegrating agent, starch, agar, gelatin powder, crystalline cellulose, calcium carbonate, sodium hydrogencarbonate, calcium citrate, dextrin, carboxymethyl cellulose, calcium and pectin; the lubricant, magnesium stearate, talc, polyethylene glycol, silica and hardened vegetable oils; the coloring, any one which is permitted for drugs; the corrigent, cacao powder, mentha herb, aromatic powder, mentha oil, borneol and powdered cinnamon bark. Of course, these tablets and granules may be, if necessary, coated with sugar, gelatin or the like.

Examples of medicine's preparation, including orally dosed preparation and that with a enteric coating of the invention including the compound (I) or (II) of the invention are shown below. These are not intended as any limitation to the invention.

EXAMPLE 1

Tablets including the compound (I):
2-[(4-(3-Methoxypropoxy)-3-methylpyridine-2-yl)-methylsulfinyl]-1H-benzimidazole were prepared by the formula below.

2-[(4-(3-Methoxypropoxy)-3-methylpyridine-2-yl)-methylsulfinyl]-1H-benzimidazole, mannitol and magnesium oxide were mixed with one another, hydroxypropylcellulose dissolved in ethanol was added to the mixture, the resultant mixture was granulated, dried and classified with a sieve of 28 mesh according to ASTM, the product being called (A). Then crystalline cellulose and corn starch were mixed with the product (A), hydroxypropylcellulose dissolved in water was added to the mixture. The resultant was granulated, dried and classified with a sieve of 28 mesh, the product being called (B). The products (A) and (B), calcium salt of carboxymethylcellulose, talc and magnesium stearate were mixed with one another and the mixture was formed into plain tablets with a single shot tablet-formulating machine, being available from Okada Seiko-sha.

Prescription in 1 plain tablet weighing 120.2 mg is shown below in unit of mg:

2-[(4-(3-Methoxypropoxy)-3-methylpyridine-2-yl)-methylsulfinyl]-1H-benzimidazole 5.0
mannitol 45.3
magnesium oxide 40.0
hydroxypropylcellulose 2.5
crystalline cellulose 10.0
corn starch 10.0
carboxymethylcelulose calcium 5.0
talc 2.0
magnesium stearate 0.2
The obtained plain tablets were coated with a enteric coating to obtain tablets.

EXAMPLE 2

Tablets including 2-[(4-(3-Methoxypropoxy)-3-methylpyridine-2-yl)-methylthio]-1H-benzimidazole (II) were prepared by the formulation below.

2-[(4-(3-Methoxypropoxy)-3-methylpyridine-2-yl)-methylthio]-1H-benzimidazole and mannitol were mixed with each other, hydroxypropylcellulose dissolved in ethanol was added to the mixture, the resultant mixture was granulated, dried and classified with a sieve of 28 mesh according to ASTM, the product being called (A). Then (A), crystalline cellulose, corn starch, calcium salt of carboxymethylcellulose, talc and magnesium stearate were mixed with one another and the mixture was formed into plain tablets with a single shot tablet-formulating machine, being available from Okada Seiko-sha.

Prescription in 1 plain tablet weighing 99.7 mg is shown below in unit of mg:

2-[(4-(3-Methoxypropoxy)-3-methylpyridine-2-yl)-methylthio]-1H-benzimidazole 5.0
mannitol 65.3
hydroxypropylcellulose 2.5
crystalline cellulose 10.0
corn starch 10.0
carboxymethylcelulose calcium 5.0
talc 2.0
magnesium stearate 0.2
The obtained plain tablets were coated with a enteric coating to obtain tablets.

What we claim:

1. A method for eradicating C. pylori resistant to macrolide or newquinolone antimicrobial agents comprising administering to a mammal suffering from a C. pylori infection resistant to macrolide or newquinolone antimicrobial agents a pharmacologically effective amount of the compound having the below shown formula (I) or (II) or a pharmacologically acceptable salt thereof

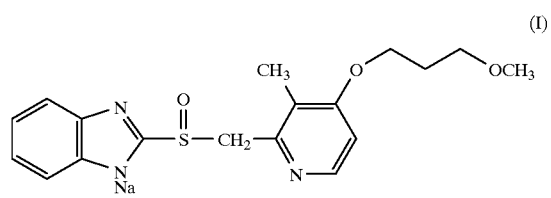

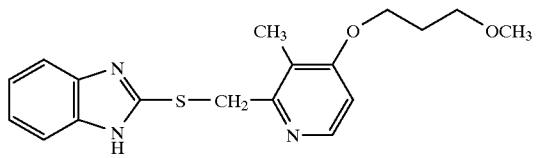
(II)

2. The method as claimed in claim 1, in which the mammal is human being.

3. A method for preventing, improving or treating a disease caused by *C. pylori* resistant to macrolide or newguinolone antimicrobial agents by administering a pharmacologically effective amount of the compound as defined in claim 1, having the formula (I) or (II), or a pharmacologically acceptable salt thereof to a mammal suffering from the disease.

4. A method for preventing recurring, of a disease caused by *C. pylori* resistant to macrolide or newquinolone antimicrobial agents by administering a pharmacologically effective amount of the compound as defined in claim 1, having the formula (I) or (II), or a pharmacologically acceptable salt thereof to a mammal suffering from the disease.

5. A method for restraining the adverse activity of *C. pylori* resistant to macrolide or newguinolone antimicrobial agents to cause a peptic disease by administering a pharmacologically effective amount of the compound as defined in claim 1, having the formula (I) or (II), or a pharmacologically acceptable salt thereof to a mammal suffering from the disease.

6. The method of claim 3 or claim 4 in which the disease caused by *C. pylori* is an ulcer.

7. The method as claimed in claim 6, in which the ulcer is a peptic ulcer.

8. The method as claimed in claim 6, in which the ulcer is a gastric ulcer.

9. The method as claimed in claim 6, in which the ulcer and gastritis are recurrent.

* * * * *